United States Patent [19]

Morozowich

[11] 4,026,919

[45] May 31, 1977

[54] PGD$_2$ SUBSTITUTED ESTERS

[75] Inventor: Walter Morozowich, Kalamazoo, Mich.

[73] Assignee: The Upjohn Company, Kalamazoo, Mich.

[22] Filed: Oct. 23, 1975

[21] Appl. No.: 625,288

[52] U.S. Cl. .......................................... 260/468 D
[51] Int. Cl.$^2$ ...................................... C07C 177/00
[58] Field of Search ............................... 260/468 D

[56] References Cited

UNITED STATES PATENTS

| 3,767,813 | 10/1973 | Samuelsson | 424/318 |
| 3,816,393 | 6/1974 | Hayashi et al. | 260/209 |

FOREIGN PATENTS OR APPLICATIONS 814,520  11/1974  Belgium .............................. 260/468

OTHER PUBLICATIONS

Fiesen et al., Reagents For Organic Synthesis, 1, pp. 86, 1229 (1967).

Primary Examiner—Robert Gerstl
Attorney, Agent, or Firm—Robert A. Armitage

[57] ABSTRACT

The p-benzamidophenyl, p-(p'-acetamidobenzamido)-phenyl, p-acetylphenyl, n-decyl, p-bromophenacyl, and α-semicarbazono-p-tolyl esters of PGD$_2$ are disclosed with the process for their preparation. These compounds are useful for the same pharmacological purposes as PGD$_2$, particularly and especially as platelet aggregation inhibitors.

4 Claims, No Drawings

PGD₂ SUBSTITUTED ESTERS

DESCRIPTION OF THE INVENTION

PGD₂ is known in the art to be a potent pharmacological agent with the structural formula:

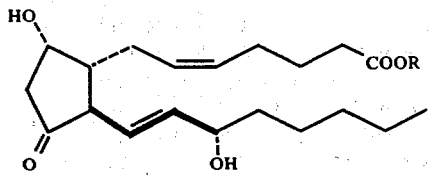

wherein R is hydrogen. See Nugteren, et al., Rec. Trav. Chim. Pays-Bas, 85, 104 (1966); Granstrom, et al., Journal of Biological Chemistry 243, 4104 (1968); C. Sih, et al., Biochem. 11, 227 (1972), Journal of Organic Chemistry 3, 38, 215 (1973); and Nishizawa, et al., Prostaglandins 9, 109 (1975); which describe the preparation and use, particularly as a platelet aggregation inhibitor, of PGD₂. Further, as is known in the art, PGD₂ is available as an oil, or is readily prepared in crystalline form. However, in either of the above physical states, but particularly when prepared with an oil, PGD₂ demonstrates significant instability. In particular, PGD₂ is subject to dehydration on the cyclopentane ring and/or double bond migrations.

However, the present invention comprises a surprising and unexpected discovery that certain esters of PGD₂ are crystalline and surprisingly and unexpectedly more stable than PGD₂, while maintaining usefulness for the same pharmacological purposes as known in the art for PGD₂. In particular, the present invention comprises the following esters of PGD₂:

a. The p-benzamidophenyl ester (R is

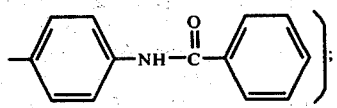

b. The p-(p'-acetamidobenzamido)phenyl ester (R is

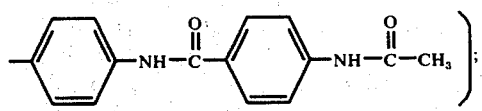

c. the p-acetylphenyl ester (R is

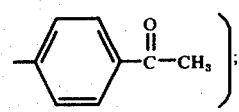

d. The n-decyl ester (R is

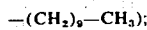

e. The p-bromophenacyl ester (R is

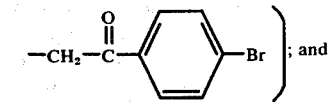

; and f. The α-semicarbazono-p-tolyl ester (R is

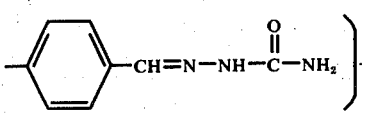

Further, there is provided by the present invention novel processes for the preparation of each of the above esters.

With respect to the use of substituted phenyl esters, the p-(p'-acetamidobenzamido)phenyl, p-benzamidophenyl, and p-acetylphenyl esters of certain prostaglandins are known in the art. See, for example, German Offenlegungsschrift No. 2,453,271 (Derwent Farmdoc CPI No. 37929W/23). Also, the n-decyl ester of certain prostaglandins is known in the art. See, for example, Belgian Pat. No. 765,641 (Derwent Farmdoc CPI No. 67533S-B) and Belgian Pat. No. 365,732 (Derwent Farmdoc CPI No. 67580S).

For the preparation of the phenacyl ester (p-bromophenacyl ester) of PGD₂ or the alkyl ester (the n-decyl ester) of PGD₂, esterification of PGD₂ proceeds by any one of various methods known in the art for preparing these esters. Thus, esterification proceeds by neutralization with sodium hydroxide, and thereafter reaction with the appropriate phenacyl or alkyl halide and solvent. The preferred method, however, is simply mixing PGD₂ with the phenacyl or alkyl halide, preferably the bromide or iodide, and a tertiary amine in a solvent and allowing the reaction to proceed at room temperature (about 20°–30° C.). The course of the reaction is readily followed by sampling the mixture and subjecting sample to thin layer chromatography, usually being complete within 15 min. to 4 hr. Thereafter the reaction mixture is worked up to yield the ester following methods described below or known in the art, for example, the product being purified by silica gel chromatography.

Examples of suitable tertiary amines are N,N-dicyclohexylethylamine, triethylamine, diethylamine, N,N-diisopropylethylamine, dimethylisobutylamine, and dimethylaniline. Examples of suitable solvents are acetonitrile, dioxane, tetrahydrofuran, N,N-dimethylformamide, and dimethylsulfoxide.

The phenacyl or alkyl halide is preferably used in equivalent amounts or in excess to insure that all of the PGD₂ is converted to the ester. Excess phenayl or alkyl halide is then separated from the product by methods known in the art or hereinbelow described, for example by silica gel chromatography.

The above solid esters are converted to free-flowing crystalline form on crystallization from a variety of solvents including ethyl acetate, tetrahydrofuran, methanol, ethanol, or acetone by cooling or evaporation of a saturated solution of the ester in a solvent or by adding a miscible non-solvent such as diethyl ether, hexane, or water. The crystals are then collected by conventional techniques, e.g. filtration or centrifugation, washed with a small amount of solvent, and dried under reduced pressure. These esters may be dried in a current of warm nitrogen or argon or by warming to about 45° C., taking care not to exceed the crystalline melting point. Although crystals are normally pure enough for many applications they may be subsequently recrystallized using the same general techniques as described above to achieve success improvements after each recrystallization.

For preparing the phenolic esters of the present invention, the p-benzamidophenyl ester, the p-(p'-acetamidobenzamido)phenyl ester, the acetylphenyl ester, and the α-semicarbazono-p-tolyl esters of $PGD_2$, there are likewise employed methods known in the art. For example, see the methods described in the above-identified German Offenlegungsschrift No. 2,453,271.

DESCRIPTION OF THE PREFERRED EMBODIMENTS

The following examples describe the methods for preparation of the esters of $PGD_2$ of the present invention.

EXAMPLE 1—$PGD_2$, p-benzamidophenyl ester

A solution of 600 mg. of $PGD_2$ and 10 ml. of acetone is treated with 0.283 ml. of triethylamine. Under a nitrogen atmosphere the solution is cooled to −10° C. and 0.267 ml. of isobutylchloroformate is added. Slow crystallization of triethylamine hydrochloride occurs and after 6 min. at −5° to 0° C. a solution of 1.08 g. of p-benzamidophenol in 5 ml. of dry pyridine is added. After 30 min. at room temperature the reaction mixture is diluted with 100 ml. of ethyl acetate and extracted twice with 100 ml. of 0.2 M aqueous phosphate buffer, pH 6.95. The organic phase is then dried with sodium sulfate and evaporation of the solvent at 45° C. under reduced pressure yields a white solid. The solid thus obtained is then stirred for 30 min. with 15 ml. of chloroform and filtered to remove most of the starting phenol. After evaporation of the filtrate, the resulting white solid is chromatographed on a silica gel column. The column is eluted with a mixture of methylene chloride, acetonitrile, and methanol (70:30:1) while collecting 25 ml. fractions. The fractions containing pure product are then cooled and removal of solvent at 40° C. under pressure yields a white solid. This white solid is then dissolved in 10 ml. of hot acetonitrile and on cooling 310 mg. of white crystals are isolated. Concentration of the filtrate yields an additional 150 mg. of product. The above lots are combined and show TLC $R_f$ of 0.5 (methylene chloride in acetonitrile, 7:3). Melting range is 152.0°–152.5° C.

EXAMPLE 2—$PGD_2$ p-(p'-acetamidobenzamido)phenyl ester

A solution of 600 mg. of $PGD_2$ in 10 ml. of dry acetone is treated with 0.83 ml. of triethylamine. Under a nitrogen atmosphere the solution is cooled to −10° C. and 0.267 ml. of isobutylchloroformate is added. Slow crystallization of triethylamine hydrochloride occurs and after 6 min. at −5 to 0° C. a solution of 919 mg. of p-(p'-acetamidobenzamido)phenol in 4 ml. of dry pyridine and 2 ml. of dimethylformamide is added. After 30 min. at room temperature the reaction mixture is diluted with 100 ml. of ethyl acetate and extracted twice with 100 ml. of 0.2 M aqueous phosphate buffer, pH 6.95. The organic phase is then dried over sodium sulfate and evaporated to yield a white solid. This white solid is then dissolved in 10 ml. of warm methanol and on cooling to room temperature crystallization of 625 mg. of a white solid occurs. Recrystallization of the compound from 15 ml. of hot methanol yields 470 mg. of product with melting range of 179.5°–182.4° C. The compound shows silica gel TLC $R_f$ of 0.6 (methylene chloride acetonitrile; 2:3).

EXAMPLES 3—$PGD_2$, p-acetylphenyl ester

A solution of 600 mg. of $PGD_2$ and 10 ml. of dry acetone is treated with 0.283 ml. of triethylamine. Under a nitrogen atmosphere the solution is cooled to −10° C. and 2.7 ml. of isobutylchloroformate is added. Slow crystallization of triethylamine hydrochloride occurs and after 6 min. at −5 to 0° C. a solution of 695 mg. of p-hydroxyacetophenone in 5 ml. of dry pyridine is added. After 30 min. at room temperature the reaction mixture is diluted 100 ml. of ethyl acetate and extracted twice with 100 ml. of 1 0.2 M aqueous phosphate buffer, pH 6.95. The organic phase is then dried over sodium sulfate and removal of the solvent at 40° C. under reduced pressure yields a tan solid which is chromatographed on a silica gel column. The column is then eluted with a mixture of methylene chloride, acetonitrile, and methanol (70:30:0.5), while collecting 25 ml. fractions. Fractions containing pure product are combined, and solvent is evaporated, yielding 65.3 mg. of a white solid. The white solid thereby obtained is dissolved in 6 ml. of ethyl acetate and diluted with 10 ml. of hexane resulting in crystallization of 355 mg. of a white compound. An additional 180 mg. of this compound is isolated by concentration of the filtrate. Both lots, containing pure title product, exhibit silica gel TLC $R_f$ of 0.4 (methylene chloride in acetonitrile, 7:3). Melting range is 81.9°–83.5° C.

EXAMPLE 4—$PGD_2$ α-Semicarbazono-p-tolyl ester

A solution of 600 mg. of $PGD_2$ and 10 ml. of acetone is treated with 0.83 ml. of triethylamine. Under a nitrogen atmosphere the solution is cooled to −10° C. and 0.283 ml. of isobutylchloroformate is added. Crystallization of triethylamine hydrochloride is initiated within one min. and after 6 min. at −5 to 0° C. a solution of 950 mg. of p-hydroxybenzaldehyde semicarbazone in 5 ml. of pyridine is added. After 15 min. at room temperature the resulting mixture is then diluted with 100 ml. of ethyl acetate. The resulting mixture is then extracted with 100 ml. of 0.2 M phosphate buffer, pH 6.95. Silica gel TLC on the organic phase indicates quantitative ester formation. The organic phase is then dried over sodium sulfate and evaporation of solvent under reduced pressure at 45° C. yields a tan solid. This tan solid is then dissolved in 25 ml. of acetonitrile and after one hr. of stirring 250 mg. of starting p-hydroxybenzaldehyde semicarbazone crystallized. After filtration, the solvent is removed under reduced pressure and the residual white solvent chromatographed on a silica gel column. The column is eluted with a mixture of acetonitrile, tetrahydrofuran, and water (50:50:2), while collecting 20 ml. fractions. Combination of fractions containing pure product and evaporation of solvent yields 815 mg. of a white solid. The white solid is dissolved in 15 ml. of hot acetonitrile and after standing in a freezer overnight, crystallization of a white solid occurs. The mixture is allowed to warm to room temperature, and 350 mg. of white crystals are isolated by filtration under a nitrogen atmosphere. Concentration of the filtrate yields an additional 450 mg. of white title product. Silica gel TLC of each of the above lots indicates

EXAMPLE 5—PGD₂ p-bromophenacyl ester

PGD$_2$ (600 mg.) is dissolved in 10 ml. of acetonitrile and treated with 0.877 ml. of N,N-diisopropylethylamine and 1.42 g. of 2,4'-dibromoacetophenone. After 2 hr. at room temperature the reaction mixture is diluted with 100 ml. of ethyl acetate and extracted twice with 100 ml. of a 0.2 M aqueous phosphate buffer, pH 6.95. The organic phase of the extract is then dried over sodium sulfate and evaporation of solvent at 40° C. under reduced pressure yields a yellow solid which is chromatographed on a silica gel column. The column is eluted with 450 ml. of methylene chloride and acetonitrile (80:20) followed by addition of 500 ml. of methylene chloride and acetonitrile (70:30) while collecting 25 ml. fractions. Fractions containing pure product are then combined and the solvent is evaporated yielding 755 mg. of a pale yellow oil. This pale yellow oil is then dissolved in 5 ml. of ethyl acetate and dilution with 10 ml. of hexane results in crystallization of 480 mg. of white compound. An additional 230 mg. of this white compound, pure title product, is obtained by concentration of the filtrate. Both samples indicate silica gel TLC $R_f$ of 0.5 (methylene chloride in acetonitrile, 70:30). The melting range is 89.8°–91.6° C.

$R_f$ of 0.6 (acetonitrile in methanol; 9:1). Melting range is 130.8°–133.7° C.

EXAMPLE 6—PGD₂ n-decyl ester

A solution of 600 mg. of PGD$_2$ in 5 ml. of acetonitrile and 2 ml. of dimethylsulfoxide is mixed with 0.877 ml. of N,N-diisopropylethylamine and 1.37 g. of iododecane. After stirring magnetically at 30° C. for 4 hr., silica gel TLC shows that about 50 percent esterification of PGD$_2$ has occurred. Additionally, the formation of a less polar impurity is noted. Thereupon the reaction mixture is diluted with 100 ml. of ethyl acetate and extracted twice with 100 ml. of 0.2 M aqueous phosphate buffer, pH 6.95. The organic phase is then dried under sodium sulfate and evaporation of solvent at 40° C. under reduced pressure yields a brown oil which is chromatographed on a silica gel column. The column is eluted with 600 ml. of a mixture of methylene chloride, acetonitrile, and methanol (70:30:0.5) followed by elution with methylene chloride, acetonitrile, and methanol (70:30:1.5), while collecting 25 ml. fractions. Fractions containing pure title product are pooled and removal of solvent yields 200 mg. of a white solid which exhibits silica gel TLC $R_f$ of 0.7 (methylene chloride in acetonitrile, 7:3). The melting range is 49.2°–54.3° C.

I claim:
1. PGD$_2$ p-benzamidophenyl ester.
2. PGD$_2$ p-(p'-acetamidobenzamido)phenyl ester.
3. PGD$_2$ p-acetylphenyl ester.
4. PGD$_2$ semicarbazono-p-tolyl ester.

* * * * *